Figure 1:
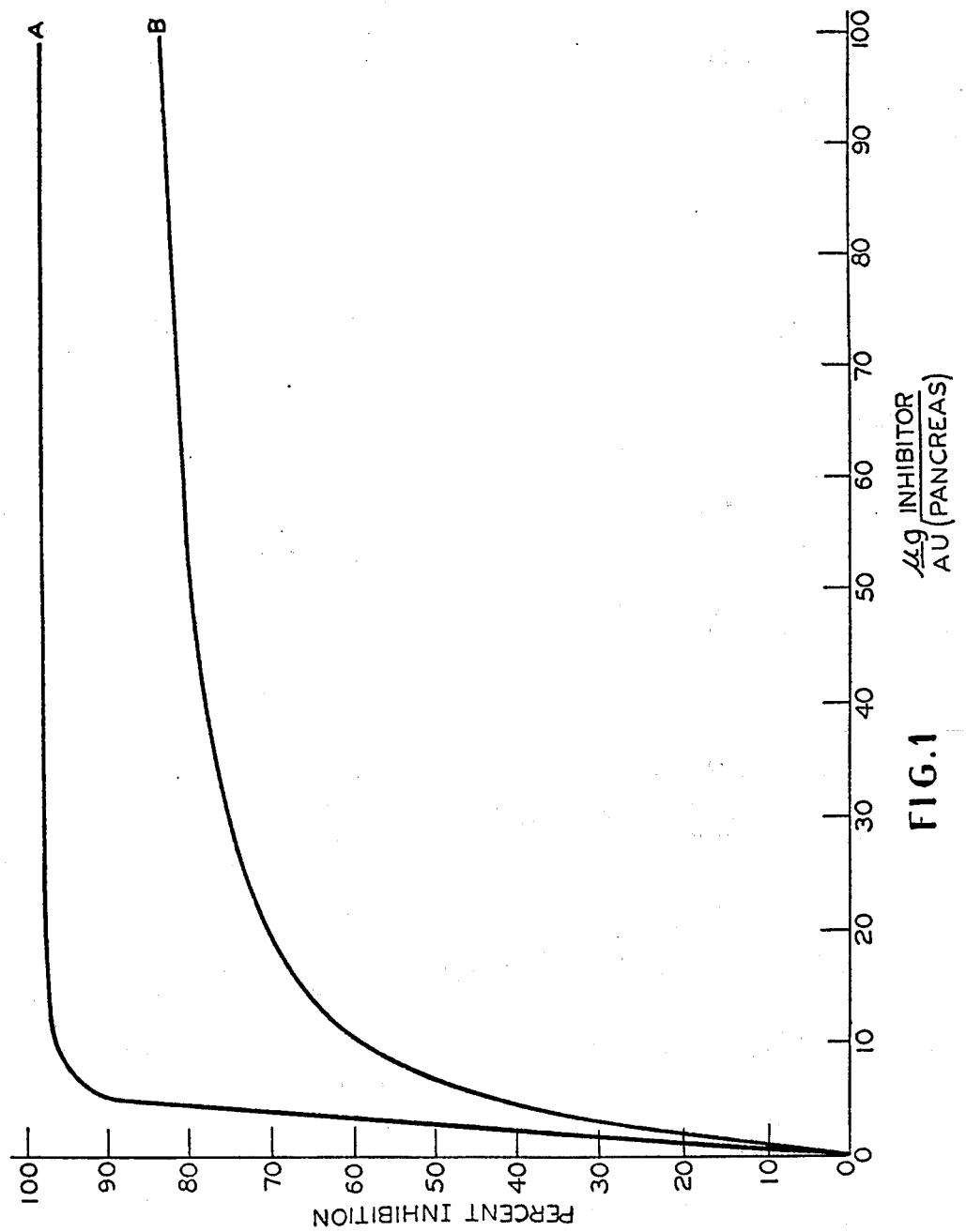

United States Patent [19]
Schmidt et al.

[11] 3,950,319
[45] Apr. 13, 1976

[54] AMYLASE INHIBITOR FROM WHEAT GLUTEN USING ALCOHOL

[75] Inventors: Delf Schmidt, Wuppertal-Vohwinkel; Walter Puls, Wuppertal-Elberfeld, both of Germany

[73] Assignee: Farbenfabriken Bayer Aktiengesellschaft, Leverkusen, Germany

[22] Filed: Jan. 23, 1974

[21] Appl. No.: 435,648

Related U.S. Application Data

[63] Continuation of Ser. No. 110,482, Jan. 28, 1971, abandoned.

[30] Foreign Application Priority Data

Jan. 29, 1970 Germany.............................. 2003934
June 11, 1970 Germany.............................. 2028739

[52] U.S. Cl............................ 260/112 G; 424/177
[51] Int. Cl.² ......................................... C07G 7/00
[58] Field of Search .............................. 260/112 G

[56] References Cited
UNITED STATES PATENTS

| | | | |
|---|---|---|---|
| 340,705 | 4/1886 | Duryea ......................... | 260/112 G |
| 2,384,388 | 9/1945 | Monte et al. ................... | 260/112 G |
| 2,448,002 | 8/1948 | Pearce ......................... | 260/112 G X |
| 2,567,980 | 9/1951 | Tuomy et al. .................. | 260/112 G X |
| 2,801,236 | 7/1957 | Miley ........................... | 260/112 G |
| 2,861,061 | 11/1958 | Borel et al. ................... | 260/112 G X |
| 3,409,440 | 11/1968 | Hohl ............................. | 99/17 |

FOREIGN PATENTS OR APPLICATIONS 708,806 5/1954 United Kingdom............. 260/112 G

OTHER PUBLICATIONS

Arch—Biochemistry, 9, pp. 235-249, (1946), Kneen et al.
Arch—Biochemistry, 9, pp. 309-320 (1946), Militzer et al.

*Primary Examiner*—Howard E. Schain
*Attorney, Agent, or Firm*—Depaoli & O'Brien

[57] ABSTRACT

An inhibitor for α-amylases, particularly pancreas amylase, is extracted from wheat, as for example, wheat flour or wheat gluten, by means of aqueous alcoholic solutions of lower alcohols of 1 to 3 carbon atoms, or dilute aqueous acid solutions having a pH of from 1 to 5, or of mixtures of the aqueous alcoholic solutions with dilute acids, and separating the desired amylase inhibitor contained in the aqueous phase from the extraction mixture by known methods. The amylase inhibitor thus obtained is particularly effective against pancreas amylase and is indicated as a therapeutic agent for the treatment of conditions resulting from alimentary hyperglycemia, such as adiposity, arteriosclerosis, diabetes and prediabetes.

5 Claims, 3 Drawing Figures

AMYLASE INHIBITOR FROM WHEAT GLUTEN USING ALCOHOL

This is a continuation, of application Ser. No. 110,482 filed Jan. 28, 1971, now abandoned.

BACKGROUND OF THE INVENTION

1. Field of the Invention

The present invention relates, in general, to an amylase inhibitor and to methods for preparing the same. More particularly, this invention is directed to a highly active inhibitor for pancreas amylase, to methods for the extraction thereof from wheat and to the application of such amylase inhibitor as a therapeutic agent for the reduction of alimentary hyperglycemia.

2. Description of the Prior Art

It is known that $\alpha$-amylases can be inhibited by various low-molecular substances, such as e.g. salicylic acid and abiscisine (T. Hemberg, J. Parsson, Physiol. Plant. 14, 861 [1961]; T. Hemberg, Acta. Checm. Scand. 21, 1665 [1967]). It is further known that there also exist substances of higher molecular weight which are capable of unspecifically inhibiting the activity of some amylases by physical adsorption (T. Chrzaszcz, J. Janicki, Bioch. Z. 260, 354 [1933] and Bioch. J. 28, 296 [1934]) or by denaturing and precipitation of the enzyme (B. S. Miller, E, Kneen, Arch. Biochem. 15, 251 [1947]; D. H. Struhmeyer, M. H. Malin, Biochem, Biophys. Acta 184, 643 [1969]). Moreover, it has been observed that it is possible to elute with distilled water from wheat a substance which reduces the dextrifying activity of saliva amylase but has little influence on the activity of pancreas amylase (E. Kneen, R. M. Sandstedt, Arch. Bioch. 9, 235 [1946]).

SUMMARY OF THE INVENTION

It is a disadvantage of the substances described above that the inhibition of the amylase is either unspecific or, as our own investigations have shown, that the inhibiting activity of the described substances is particularly poor in relation to pancreas amylase; that is to say, that almost complete inhibition of the amylases (up to 90% and more) is only achieved with a very high ratio of inhibitor to enzyme (cf. FIG. 1; this shows the inhibition course of the amylase inhibitor according to the invention [curve A] in comparison with an inhibitor prepared according to the instructions given by Kneen [1946 loc. cit.] [curve B] in relation to 2.13 amylase units [AU] of pancreas amylase).

It has now been found that it is possible to extract a highly active inhibitor for pancreas amylase which does not have the aforesaid disadvantages, from wheat (shredded wheat, wheat flour or gluten) with the aid of aqueous electrolyte solutions, preferably dilute acids or, primarily, water/alcohol ($C_1$-$C_3$-alcohols) mixtures, preferably at acid pH values. The substance so obtained inhibits pancreas amylase even at a very low ratio inhibitor:enzyme to the extent of more than 90% (FIG. 1). The same substance also inhibits saliva amylase to a high degree. Other hydrolases (in so far as they have been tested), e.g. trypsin, pepsin, chymotrypsin and ribonuclease, are not inhibited by this inhibitor.

The gluten mentioned, inter alia, above as starting material is the protein component of wheat and is obtained as a by-product in the productor of wheat starch (Hagers Handbuch der pharmazeutischen Praxis, Vol. I, [Verlag Julius von Springer, Berlin, 1925, page 332]; M. J. Blish in M. L. Anson, J. T. Edsall, Advances in Protein Chemistry, Vol. II, [Academic Press, New York, 1945, page 337]).

Figure 2:
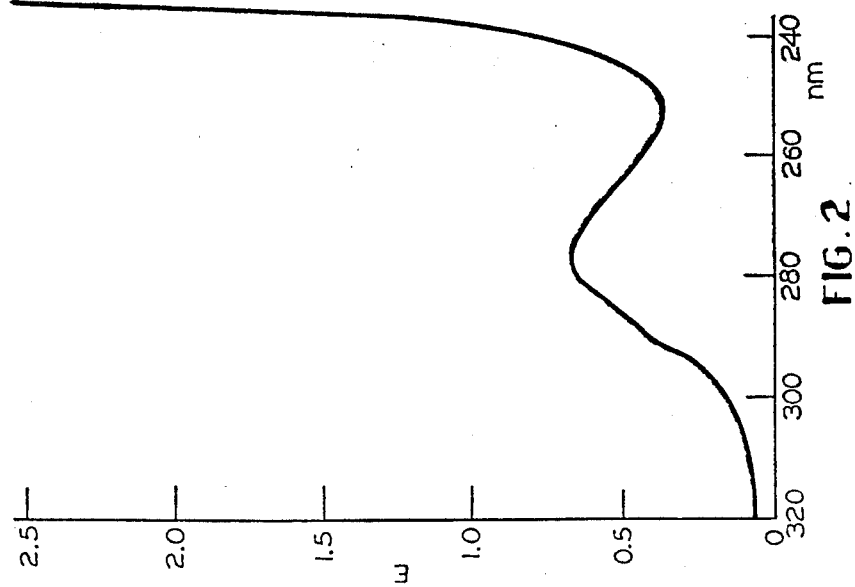

The new substance is colorless and dissolves readily in water, dilute acids and alkaline solutions as well as in aqueous alcohols. The u.v. absorption spectrum of a 0.1% aqueous solution of the inhibitor is shown in FIG. 2. The absorption maximum lies at 278 nm. The substance is insoluble in ether, acetone and absolute alcohols. The new inhibitor cannot be dialysed. The substance can be precipitated with 2–5% trichloroacetic acid; the precipitate is soluble in $H_2O$ and still exhibits 60 to 80% of its initial activity. The substance is slowly inactivated by proteases (pepsin, trypsin, chymotrypsin). Solutions of the substance are comparatively stable to acid (up to pH 1 to 2), but labile to alkali; incubation at 37°C. in 0.15 m $Na_2CO3$ at pH 11.4 leads to an 80% loss of activity. Neutral aqueous solutions of the inhibitor are stable up to temperatures of 85°C. From 90°C., however, inactivation of the amylase inhibitor occurs and rapidly increases as the duration of incubation is increased (measured in 0.02 m glycerophosphate/0.001 m $CaCl_2$ buffer, pH 6.9). By the addition of urea up to a concentration of 2 mol/liter the inhibitor is not inactivated, up to 8 mol/liter it is inactivated to 50 – 60%. According to these findings, the amylase inhibitor is a polypeptide.

The inhibiting capacity of the best inhibitor preparations in relation to pig pancreas amylase amounts to 700 to 800 pancreas amylase inhibitor units (pancreas AIU), per mg, in relation to saliva amylase to 900 to 1000 saliva amylase inhibitor units (saliva AIU) per mg. The high activity of this inhibitor also against pancreas amylase (FIG. 1, curve A) distinguishes the inhibitor from that described by Kneen (Arch. Biochem. 9, 235 [1946]) (FIG. 1, curve B), which inhibits saliva amylase with about half the capacity of 500 saliva AI-U/mg inhibitor, but has only a poor activity against pancreas amylases (below 10 pancreas AIU/mg) and can inhibit hardly more than 80% of the pancreas amylase activity even if added in large amounts (FIG. 1, curve B).

One amylase inhibitor unit (1 AIU) is defined as the amount of inhibitor which inhibits one amylase unit to 90% (a 90% inhibition was chosen because of easier interpolation when determining the inhibition capacity). Complete inhibition is achieved asymptotically (cf. FIGS. 1 and 3). One amylase unit is the amount of enzyme which splits 1 $\mu$ equivalent of glucosidic bonds in starch within one minute under the below stated test conditions. The $\mu$ gram equivalent of split bonds are colorimetrically determined with dinitrosalicylic acid as $\mu$ gram equivalent of reducing sugars formed and are stated as $\mu$ gram equivalent maltose equivalents with the aid of a maltose calibration curve.

To carry out the test, 0.1 ml. of amylase solution (20 to 22 AU/ml) are mixed with 0 to 400 $\mu$g inhibitor in 0.4 ml of 0.02 m sodium glycerophosphate buffer/0.001 m $CaCl_2$, pH 6.9, and equilibrated on a water bath of 35°C. for about 10 to 20 minutes. The mixture is then incubated at 35°C. for 5 minutes with 0.5 ml of a 1% starch solution (starch, soluble, manufacturers Merck, Darmstadt, No. 1252) which has been preheated to 35°C., and subsequently mixed with 1 ml of dinitrosalicylic acid reagent (according to P. Bernfeld in Colowick-Kaplan, Meth. Enzymol, Vol. 1, page 149). To develop the color, the mixture is heated on a boiling water bath for 5 minutes, it is then cooled and 10 ml of distilled water are added. The extinction at 540 nm is measured against a blank value correspondingly prepared without amylase. For evaluation, the amylase activity which is still effective after addition of the inhibitor is read from a previously plotted amylase calibration curve, and the percentage inhibition of the amylase used is calculated therefrom. The percentage inhibition is plotted as a function of the quotient $$\frac{\mu g \text{ inhibitor}^+}{AU^{++}}$$

+ referred to dry substance
++ AU in the non-inhibited mixture of the same series (cf. FIG. 1), the 90% inhibition point is read from the curve and recalculated for AIU/mg inhibitor.

The extraction of the inhibitor according to the invention from wheat flour, shredded wheat or gluten is carried out according to the invention either (A) with 10 to 90%, preferably 30 to 70% water/alcohol mixtures (water-soluble lower alcohols such as methanol, ethanol, propanol or isopropanol); or (B) with dilute aqueous electrolyte solutions, preferably dilute aqueous acids, at pH values of 1 to 5, preferably at pH values of 2 to 4; or (C) with water/alcohol mixtures of the composition stated under (A) but at acid pH values of 1 to 6, preferably 2 to 4 (in the presence of mineral acids or organic acids).

Figure 3:
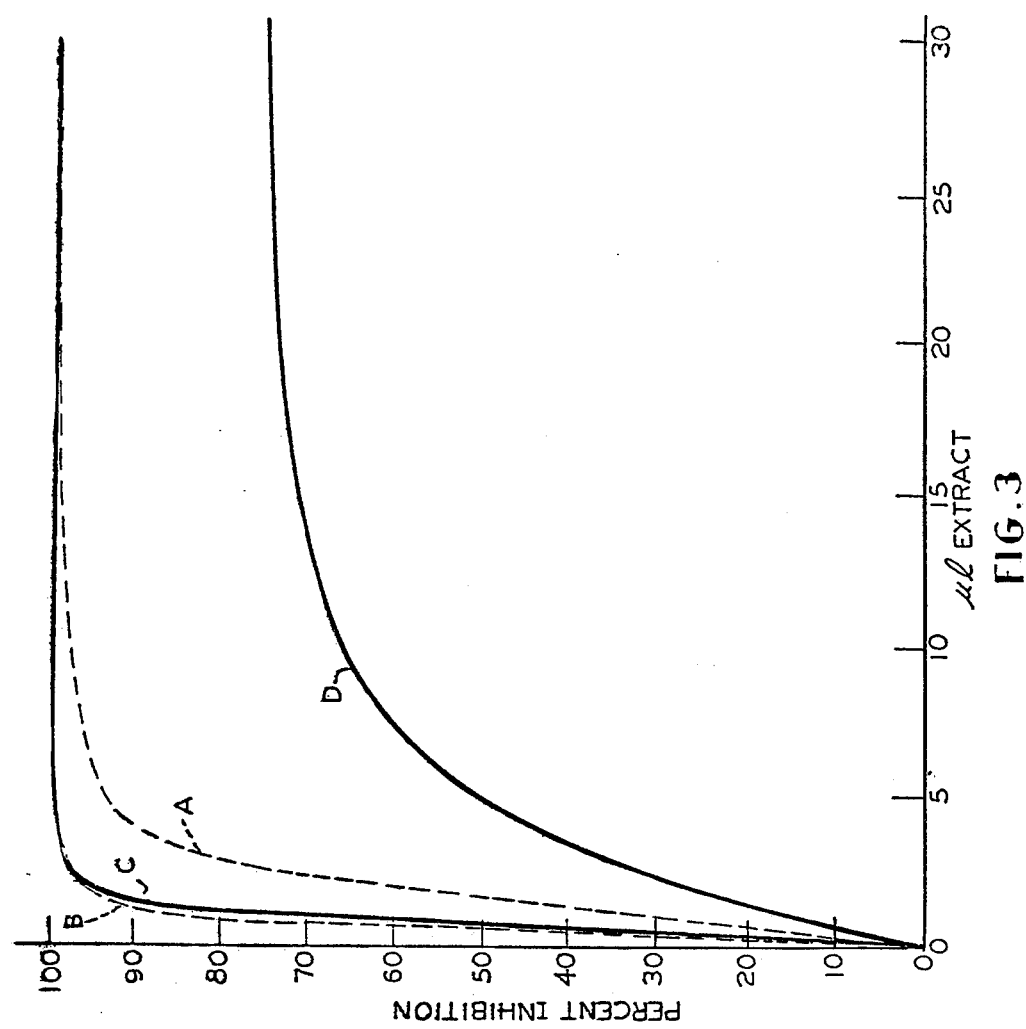

For this purpose, 1 part by weight of wheat flour, shredded wheat or gluten is homogenized with 1.5 to 5 parts by weight, preferably 2 to 4 parts by weight, of the appropriate extraction medium for 1 to 2 minutes and the mixture is subsequently stirred for ½ to 4 hours (preferably 1 to 2 hours) at room temperature (20° to 25°C.). The mixture is then filtered or centrifuged at 3000 to 10000 g for 10 to 20 minutes. If desired, the residue is reextracted with 1 to 2 parts by weight of the extraction medium, as described above, and centrifuged or filtered. The supernatant solutions or filtrates are combined; in the case of acidic extraction, they are neutralised, preferably with a concentrated ammonia solution, and freed from the ballast proteins precipitated in the course of neutralisation by filtration or centrifuging. In contrast to aqueous wheat flour extracts which are capable of very effectively inhibiting saliva amylases but not pancreas amylases (FIG. 3, curve D), the extracts prepared according to the invention by the methods (A) to (C) show an extraordinarily high inhibiting activity also against pancreas amylases (FIG. 3, curves A,B,C,). FIG. 3 illustrates the inhibition of 2.2 AU pig pancreas amylase by (A) a 66% ethanolic, (B) an acidic aqueous (pH 3), (C) a 30% aqueous ethanolic (pH 3) and (D) an aqueous neutral extract from wheat flour. In each case, 1 part by weight of wheat flour was extracted with 4 parts by weight of extraction agent at 20°C. for 1 hour.

The preferred process for the production of the amylase inhibitor according to the invention is the extraction of wheat flour or gluten with acidic aqueous alcohols (30 to 70% methanol or ethanol, pH 2 to 4) (process C). This method gives higher yields of inhibitor than the extraction process with neutral aqueous alcohols (process A); compared with the acidic aqueous extraction mixtures (process B), it has the advantage that the mixture is less viscous and therefore easier to handle for stirring, contrifuging or filtration. Moreover, the coextraction observed in processes (A) and (B), of an amylase which is present in wheat flour and cannot be inhibited is obviated in this process and inactivation or separation of the vegetable amylase is therefore unnecessary.

When gluten is used as starting material, the yields are 5 to 8 times higher than with the use of wheat flour. Another advantage consists in that the extraction mixtures are easier to filter and centrifuge and that the amylase inhibitor is obtained with a higher specific activity when gluten is used as starting material.

Isolation of the inhibitor from the extraction solutions (which are previously neutralised in processes B and C) can be carried out in various ways:

a. Concentration of the extracts under reduced pressure (10 to 20 mm Hg) at temperatures up to 40°C. to about 1/5 to 1/10 of the starting volume. The concentrated extract is filtered or centrifuged and the clear filtrate (or the clear supernatant solution) is lyophilized after desalting.

b. Precipitation of the inhibitors from the extracts with the aid of acetone. This process is mainly suitable for extracts still having a high content of alcohol (alcohol concentration above 60%), since relatively complete precipitations with the aid of volumes of acetone which are not too high can only be attained from such extracts. The precipitation is achieved by pouring 1 part by volume of the solution to be precipitated into 2 to 4 parts by volume acetone (depending upon the alcohol content of the extraction solution to be precipitated). Drying of the suction-filtered inhibitor preparation in a vacuum at room temperature after washing with absolute alcohol.

c. Precipitation of the inhibitors from the extracts (or the extracts concentrated according to [a]) by the addition of lower alcohols up to a per cent by volume content of 95 for ethanol, 90 for n-propanol or 80 for isopropanol. The amylase inhibitor can also be precipitated with 95% methanol, but in lower yields than are obtained with the use of aforesaid alcohols.

Since low alcohol concentrations lead to the precipitation of inactive accompanying substances (e.g. proteins), the precipitation process is also suitable for fractional precipitation.

d. Salting out of the amylase inhibitor from the extracts (or from the extracts concentrated according to [a]). e.g. with sodium chloride, ammonium sulphate etc. e. Precipitation of the amylase inhibitor from extracts with a certain alcohol content at low temperatures. For this purpose, the extracts are first adjusted to alcohol concentrations of 10 to 50%, preferably 20 to 40%, and subsequently kept for several hours (8 to 24 hours) at below 0°C., preferably at −10°to −20°C. The inhibitor settles well and the clear supernatant liquid can be drawn off. The remaining precipitate is centrifuged off at −10°to −20°C. One part by volume of the sediment is immediately washed with about 10 parts by volume of absolute ethanol or about 5 parts by volume of absolute isopropanol, preferably in the cold (0°C.), and subsequently dried at room temperature, preferably in a vacuum. This method is also suitable for fractional precipitation at different temperatures.

It is known that after the intake of carbohydrate-containing food (cereal starch, potato starch) alimentary hyperglycemiae occur in animals and humans; this is caused by a rapid decomposition of the carbohydrates by amylase (saliva and pancreas amylase) and maltase according to the following scheme

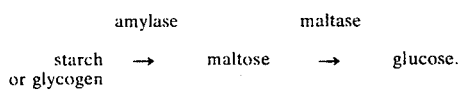

$$\text{starch or glycogen} \xrightarrow{\text{amylase}} \text{maltose} \xrightarrow{\text{maltase}} \text{glucose.}$$

These hyperglycemiae are particularly marked and persistent in diabetics. In adipose persons the alimentary hyperglycemia frequently gives rise to a particularly strong secretion of insulin which in turn leads to increased formation of fat and reduced decomposition of fat.

It has been found that the amylase inhibitor according to the invention, isolated by the above methods, significantly reduces alimentary hyperglycemia in six healthy test persons after loading with wheat starch (see Experiment Example 5 below). It is therefore suitable as therapeutic agent for

| Indications: | adiposity, arteriosclerosis, diabetes and prediabetes; |
|---|---|
| Dosage: | 5,000 to 1,000,000 AIU once or several times daily per os before and/or during meals; |
| Forms of Preparation: | tablet, dragee, solution, suspension, granules and as additive to starch-containing food. |

The toxicity of this inhibitor is low. $1.7 \times 10^6$ AIU/kg mouse per os were tolerated without symptons.

Combinations with the known oral antidiabetes (B-cytotropic sulphonyl-urea derivatives and/or blood sugar depressing biguanides) are also of advantage.

The following examples are illustrative of the extraction methods and therapeutic effects of the present invention.

EXAMPLE 1

1 kg of wheat flour is homogenized with 2 liters of 66% ethanol, pH 3 to 3.5, adjusted to pH 3 to 3.5 with NCl, and stirred at room temperature for 30 minutes. The mixture is then centrifuged at 6000 r.p.m. for 10 minutes (20°C.), the supernatant liquid is stored and the residue is reextracted as described above with a further 2 liters of 66% ethanol at pH 3 to 3.5. The combined supernatant liquids are neutralised with concentrated ammonia and the flocculated ballast proteins are removed by centrifuging (6000 g, 10 minutes). The clear slightly yellowish supernatant liquid (2.8 liters) is concentrated to ~1/10 of its volume (300 ml) at about 20 mm Hg and a bath temperature of 40° to 59°C., again freed from precipitated proteins by centrifuging and after 8 hours' dialysis against distilled water at room temperature, it is frozen and lyophilized.

Yield: 10 g with 140,000 pancreas AIU/g lyophilisate ($\hat{=}$ 7.5 g inhibitor dry substance with 185,000 pancreas AIU/g).

EXAMPLE 2

1 kg of wheat flour is homogenized with 4 liters of 30% ethanol in a starmixer, adjusted to pH 3 to 3.5 with hydrochloric acid and stirred at room temperature for 60 minutes. The mixture is centrifuged at 6000 r.p.m. for 10 minutes, the supernatant liquid is adjusted with concentrated ammonia to pH 6.8 and centrifuged off from the ballast proteins. The clear supernatant liquid is stored overnight at −15°C., the supernatant clear solution is decanted off and the precipitated sediment is subsequently collected in pre-cooled centifuging glass vessels at −15°C., (Zeta 20 cooling centrifuge, 10 minutes, 6000 r.p.m.). It is mixed with ice-cold absolute ethanol (room temperature from now on), washed with absolute alcohol and dried in a vacuum drier.

Yield: 10 g with 160,000 pancreas AIU/g (= 8g inhibitor dry substance with 200,000 pancreas AIU/g).

EXAMPLE 3

200 g of flour are homogenized with 800 ml of water, adjusted with HCl to pH 3.3 and stirred at room temperature for 30 minutes. The mixture is subsequently centrifuged for 30 minutes at 10,000 g, the turbid supernatant liquid is neutralised with NH₃ and again centrifuged at 10,000 g for 30 minutes.

The 600 ml of turbid supernatant liquid are mixed with 1100 ml of absolute alcohol, filtered and the inhibitor is precipitated from the filtrate with a further 5 liters of absolute ethanol. It is washed with absolute ethanol and dried in a vacuum.

Yield: 1.5 g with 90,000 pancreas AIU/g lyophilisate.

EXAMPLE 4

500 g of wheat flour are homogenized with 2 liters of 75% methanol for 2 minutes, stirred at room temperature for 1 hour and subsequently filtered through two large fluted filters. The clear filtrate (1.6 liters) is added dropwise with stirring to 4 parts by volume (6.4 liters) acetone. The inhibitor settles at the bottom in the form of thick white flakes. The clear supernatant liquid is decanted and the white sediment is taken up in absolute ethanol, washed and finally dried at room temperature.

Yield: 12 g with 40,000 pancreas AIU/g.

EXAMPLE 5

The antihyperglycemic effect of the amylase inhibitor was tested in the following test arrangement:

100 g of cereal starch were administered in the form of an aqueous suspension per os to 6 healthy test persons. The blood sugar was determined immediately before the start of the test and at short intervals until 3 hours after application of the starch by means of the Autoanalyzer/Technicon according to Hoffman, J. Biol. Chem. 120, 51 (1937). In two further tests, the amylase inhibitor taken up in tragacanth slime was applied in the same test arrangement to the same six test persons per os immediately before application of the starch.

Change of blood glucose as % of initial value, of six healthy test persons (mean value ± 1 s) at different times after oral administration of wheat starch after previous application of the amylase inhibitor.

| | 15 | 30 | 45 | 60 | 90 | 120 | 180 min. |
|---|---|---|---|---|---|---|---|
| Control test with 100 g starch | +22±13 | +43±12 | +35±17 | +22±25 | +23±14 | +14±9 | +4±7 |
| 55 000 AIU + 100 g starch | +2±7 | +22±13 | +23±16 | +17±20 | +16±19 | +13±11 | −5±4 |

-continued

Change of blood glucose as % of initial value, of six healthy test persons (mean value ± 1 s) at different times after oral administration of wheat starch after previous application of the amylase inhibitor.

| | 15 | 30 | 45 | 60 | 90 | 120 | 180 min. |
|---|---|---|---|---|---|---|---|
| 1100 000 AIU + 100 g starch | +13±6 | +12±10 | +11±14 | +13±13 | +11±8 | +8±6 | +5±4 |

—— = P < 0.01 as against control test
═ = P < 0.001 as against control test
------ = P < 0.05 as against control test

EXAMPLE 6

10 kg wheat gluten (e.g. "Weizenkleber vital", manufacturers Crespel and Dieters, Ibbenbüren, Westphalia) were introduced in portions with intense stirring into 50 liters of 30% methanol. The mixture was then adjusted with semi-concentrated hydrochloric acid to pH 3.5; the viscosity of the solution increased temporarily. The mixture was stirred for 45 minutes and subsequently neutralised with semi-concentrated ammonia. Flocculation occurred. The mixture was centrifuged for 10 minutes at about 2000 r.p.m. and the clear centrifugate was cooled to −10°C. The precipitate flocculating in the cold settled well over night. The supernatant clear solution was decanted, the sediment collected in a cooling centrifuge at −5°C. and, after washing with alcohol and ether, dried in a vacuum at room temperature.

Yield: 180 g with 775,000 pancreas AIU/g inhibitor.

What is claimed is:

1. A process for the production of an amylase inhibitor which comprises extracting wheat gluten with an aqueous solution containing from 10% up to about 90% of an alcohol of from 1 to 3 carbon atoms in a mixture with a dilute acid and having a pH from 2 to 4, and separating the amylase inhibitor contained in solution from the extraction mixture; and wherein said amylase inhibitor on a dry weight basis has an inhibiting capacity in relation to pancreas amylase of 700 to 800 pancreas amylase inhibitor units (pancreas AIU) per mg, and in relation to saliva amylase of 900 to 1000 saliva amylase inhibitor units (saliva AIU) per mg.

2. A process for the production of an amylase inhibitor which comprises extracting a member of the group consisting of wheat flour, shredded wheat and gluten with a member of the group consisting of (A) an aqueous solution containing from 10% up to about 90% of an alcohol of from 1 to 3 carbon atoms, and (B) mixtures of aqueous alcohol solutions as defined in (A) with dilute acids and having a pH from 1 to 6, and separating the amylase inhibitor contained in solution from the extraction mixture; and wherein said amylase inhibitor on a dry weight basis has an inhibiting capacity in relation to pancreas amylase of 400 to 800 pancreas amylase inhibitor units (pancreas AIU) per mg.

3. A process for the production of an amylase inhibitor which comprises extracting wheat gluten with an aqueous solution containing 30% methanol adjusted to a pH of about 3.5, and separating the amylase inhibitor contained in solution from the extraction mixture; and wherein said amylase inhibitor on a a dry weight basis has an inhibiting capacity in relation to pancreas amylase of 700 to 800 pancreas amylase inhibitor units (pancreas AIU) per mg, and in relation to saliva amylase of 900 to 1000 saliva amylase inhibitor units (saliva AIU) per mg.

4. The amylase inhibitor derived from wheat in accordance with the process of claim 1, said amylase inhibitor being a colorless polypeptide readily soluble in dilute acids, alkaline solutions and aqueous alcohol, and having the UV absorption spectrum of 0.1% aqueous solution as shown in FIG. 2 of the accompanying drawing, and said amylase inhibitor being inactive against trypsin, chymotrypsin, pepsin and ribonuclease.

5. The amylase inhibitor produced by the process as defined by claim 3.

* * * * *

UNITED STATES PATENT OFFICE
CERTIFICATE OF CORRECTION

Patent No. 3,950,319      Dated April 13, 1976

Inventor(s) Delf Schmidt et al

It is certified that error appears in the above-identified patent and that said Letters Patent are hereby corrected as shown below:

Column 5, line 28, "symptons" should be --symptoms--.

Column 6, line 14, "(=8g inhibitor...)" should be --($\triangleq$8g inhibitor...)---.

Column 5, line 39, "NCI" should be --HCI--.

Column 7, in the chart, "1100000 AIU + 100 g starch" should be --110000 AIU + 100 g starch--.

Column 8, line 25, "400" should be --40--.

Signed and Sealed this

Seventeenth Day of August 1976

[SEAL]

Attest:

RUTH C. MASON
*Attesting Officer*

C. MARSHALL DANN
*Commissioner of Patents and Trademarks*